(12) United States Patent
Haines

(10) Patent No.: US 10,159,437 B2
(45) Date of Patent: Dec. 25, 2018

(54) SURGICAL GOWN CONFIGURED FOR PREVENTION OF IMPROPER MEDICAL PROCEDURES

(75) Inventor: Kimberly M. Haines, Deerfield, IL (US)

(73) Assignee: Medline Industries, Inc., Northfield, IL (US)

( * ) Notice: Subject to any disclaimer, the term of this patent is extended or adjusted under 35 U.S.C. 154(b) by 1067 days.

(21) Appl. No.: 13/005,778

(22) Filed: Jan. 13, 2011

(65) Prior Publication Data

US 2011/0107494 A1    May 12, 2011

Related U.S. Application Data

(63) Continuation-in-part of application No. 12/008,818, filed on Jan. 14, 2008, now Pat. No. 7,886,742.

(51) Int. Cl.

| | |
|---|---|
| *A61B 46/23* | (2016.01) |
| *A61B 5/00* | (2006.01) |
| *A61B 50/30* | (2016.01) |
| *A61B 46/00* | (2016.01) |
| *A61B 90/94* | (2016.01) |
| *A61B 5/117* | (2016.01) |
| *A61B 46/20* | (2016.01) |
| *A61B 90/00* | (2016.01) |

(52) U.S. Cl.
CPC .............. *A61B 5/411* (2013.01); *A61B 46/00* (2016.02); *A61B 50/30* (2016.02); *A61B 90/94* (2016.02); *A61B 5/117* (2013.01); *A61B 46/23* (2016.02); *A61B 2046/205* (2016.02); *A61B 2090/0807* (2016.02)

(58) Field of Classification Search
CPC ..................................................... A61M 25/02
USPC ........................ 128/846, 849, 853, 854; 2/69
See application file for complete search history.

(56) References Cited

U.S. PATENT DOCUMENTS

| | | | |
|---|---|---|---|
| 3,826,253 A | 7/1974 | Larsh et al. | |
| 4,027,665 A * | 6/1977 | Scrivens | ........................ 128/854 |
| 4,373,214 A * | 2/1983 | Wichman | ............................ 2/51 |
| 4,857,713 A | 8/1989 | Brown | |
| 4,947,867 A * | 8/1990 | Keeton | ......................... 128/846 |
| 6,382,212 B1 | 5/2002 | Borchard | |

(Continued)

OTHER PUBLICATIONS

"PCT Written Opinion and Search Report", PCT/US2012/020337; filed Jan. 5, 2012; dated Aug. 9, 2012.

*Primary Examiner* — Tarla Patel
(74) *Attorney, Agent, or Firm* — Philip H. Burrus, IV

(57) ABSTRACT

A surgical gown (100) includes a body-covering portion (101) and, optionally, sleeves (102,103). A surgery procedure verification card (120) can be attached to the surgical gown (100). The surgery procedure verification card (120), which can be configured to be selectively detachable from the surgical gown (100), is configured to facilitate a start of a surgical procedure after completion of a predetermined procedure. The surgical gown (100) can be color coded to indicate a barrier level or the presence of the surgery procedure verification card (120). The surgical gown (100) can be included in a surgical pack (400). The surgical pack (400) can include one or more surgical procedure gowns (401,402) that are not color-coded, as well as a surgical drape (440). Methods of using and manufacturing the surgical gown (100) are also described.

36 Claims, 9 Drawing Sheets

(56) References Cited

U.S. PATENT DOCUMENTS

| | | | |
|---|---|---|---|
| 6,955,002 B2 | 10/2005 | Sandel et al. | |
| 7,205,449 B2 * | 4/2007 | Levin | 602/58 |
| 7,802,313 B2 * | 9/2010 | Czajka | 2/51 |
| 7,815,123 B2 * | 10/2010 | Conner et al. | 235/487 |
| 2002/0179094 A1 * | 12/2002 | Perlow | 128/897 |
| 2003/0182815 A1 | 10/2003 | Carlson, II | |
| 2003/0187458 A1 | 10/2003 | Carlson, II | |
| 2004/0056477 A1 | 3/2004 | Bruce | |
| 2004/0056478 A1 | 3/2004 | Bruce | |
| 2005/0183182 A1 | 8/2005 | Kennan | |
| 2005/0268505 A1 | 12/2005 | Sandel et al. | |
| 2006/0096877 A1 | 5/2006 | Khajavi et al. | |
| 2008/0066215 A1 * | 3/2008 | Thompson | 2/175.5 |
| 2009/0178685 A1 | 7/2009 | Haines et al. | |
| 2009/0320177 A1 | 12/2009 | Lin et al. | |
| 2010/0017938 A1 * | 1/2010 | Shultz et al. | 2/114 |
| 2010/0050314 A1 | 3/2010 | Oleyar et al. | |
| 2010/0319712 A1 | 12/2010 | Czajka | |

* cited by examiner

SURGICAL GOWN CONFIGURED FOR PREVENTION OF IMPROPER MEDICAL PROCEDURES

CROSS REFERENCE TO PRIOR APPLICATIONS

This application is a continuation-in-part of U.S. application Ser. No. 12/008,818, filed Jan. 14, 2008, which is incorporated herein by reference for all purposes.

BACKGROUND

Technical Field

This invention relates generally to medical gowns, and more particularly to a gown configured to facilitate prevention of improperly performed medical procedures.

Background Art

Healthcare facilities are increasingly concerned about the occurrence of errors in medical and surgical procedures. As a result, more attention is being turned to the activities of the medical personnel prior, such as a surgeon and operating staff, prior to the commencement of a procedure, such as surgery. Some healthcare facilities request medical professionals to check and double check certain conditions, such as whether the proper procedure is being performed or whether the patient undergoing the procedure is the same patient for which the procedure was scheduled. Despite these warnings, it can some times be difficult to remember to check and double check each condition.

It would be advantageous to have equipment configured to prevent the start of a medical procedure until each of the checks was complete.

Figure 1:
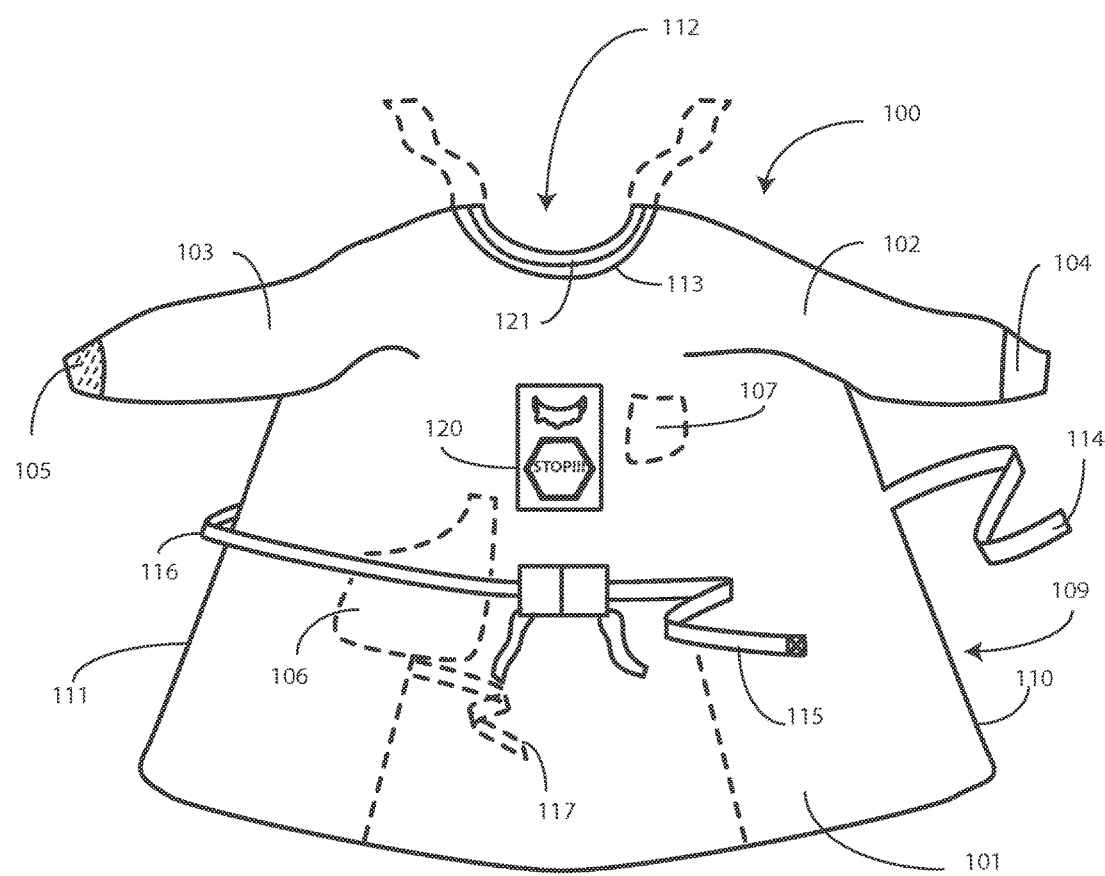
FIG. 1 illustrates a front view of one embodiment of a medical gown configured in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF EMBODIMENTS OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

In medical procedures such as surgery, professionals are implementing "pause procedures" in an effort to reduce or eliminate the occurrence of errors. These procedures, often known as a medical or surgical "time out," are procedural pauses required to call attention to final safety checks that should be completed before beginning of a medical procedure such as surgery. These time outs are called to ensure that the correct medical procedure is going to be performed on the correct patient, at the correct site, using correct supplies, and on the correct side of the patient. To this end, some national organizations, such as The Joint Commission, have prepared a set of National Patient Safety Goals to promote specific improvements in patient safety. This particular group has developed "Universal Protocols" for preventing wrong site, wrong procedure and wrong person surgeries and other medical procedures.

Unfortunately, some staff are less than vigilant in following these protocols. Moreover, some medical personnel and health care staff even resist the safety checks by performing only a portion of the protocol or ignoring the protocol completely. Where a surgeon or other medical professional fails to participate in, or encourage the use of, a time out procedure, pressure is applied to the remaining staff. Particular pressure may be applied to the circulating nurse, as he is often responsible for making sure the time out is both complied with and properly documented when complete. He generally must do this prior to the commencement of the procedure, e.g., prior to the surgeon making an incision. Embodiments of the present invention provide a medical tool that can help ensure that both steps are completed accurately.

Embodiments of the present invention include a medical gown that has a procedure verification card attached thereto. For simplicity of discussion, surgery will be used as an illustrative example of one medical procedure for which embodiments of the invention are useful. However, those of ordinary skill in the art having the benefit of this disclosure will readily recognize that surgery is just one type of medical procedure and that embodiments of the invention are well suited to any number of other non-surgical, medical procedures. Accordingly, the adjective "medical" can be substituted for the adjective "surgical" when referring to embodiments described herein. For example, when referring to a "surgical gown," it is to be understood that this refers to a "medical gown" that can be used in either surgical procedures or other non-surgical, medical procedures. Similarly, a "surgery procedure verification card" can be interpreted as a "medical procedure verification card" when used in conjunction with non-surgical, medical procedures.

The surgery procedure verification card, in one embodiment, is removably attached to a surgeon's surgical gown and is configured to facilitate the start of a surgical procedure in accordance with a predetermined procedure. In one embodiment, the predetermined procedure is a time out procedure that includes a list of conditions that must be completed and/or documented prior to the start of the surgical procedure. Illustrative conditions or steps include confirming the correct surgical site, confirming the correct surgical procedure, confirming the correct patient, and confirming the correct portion of the patient upon which the surgery should be performed. By employing embodiments of the present invention, medical personnel such as the circulating nurse will have more control in making sure the time out is properly completed. Additionally, embodiments described herein provide a checklist and verification tool. Further, since the surgery procedure verification card is coupled to the surgeon's gown in one embodiment, compliance is further encouraged due to the fact that the surgeon will not be able to finish the gowning process without removing the surgery procedure verification card. Once the time out process is completed, embodiments of the invention contemplate placement of process verification indicators in the patient's medical records.

In one embodiment, the surgical gown having the surgery procedure verification card attached thereto is marked with a color-coding indicative of the card's attachment. For example, in one embodiment, a neck binding is coupled to the body of the surgical gown and is color-coded to indicate that the surgery procedure verification card is attached to that particular surgical gown. Where the surgical gown is a surgeon's gown and is packaged with one or more surgical procedure gowns, the circulating nurse can easily identify the surgeon's gown by the color-coded neck binding. Additional color-coding can indicate a barrier level afforded by the gown as well. In one additional embodiment, cuffs coupled to the surgical gown can be correspondingly color-coded. Color-coding provides easy visual recognition when gown is folded up in a package and ready for use, or when mixed in with several other gowns within a surgical bundle.

Turning now to FIG. 1, illustrated therein is one surgical gown 100 configured in accordance with embodiments of the invention. A body-covering portion 101 is configured to wrap about the torso of a wearer, which in one embodiment will be a surgeon. As noted above, a "surgical gown" 100 is only a subset of the medical gowns in accordance with which embodiments of the invention can be configured. In other embodiments, the gown can be configured as any of a doctor's gown, a physician's gown, or a nurse's gown. It should be understood that a "surgical gown" is merely a subset of the medical gowns that can be designed in accordance with the description herein.

In one embodiment, the surgical gown 100 is manufactured from a non-woven fabric. Examples include spunlace, spunbond, and blends of polyester, polypropylene, and/or polyethylene, as well as combinations thereof. Suppliers of such materials include Cardinal Health in Dublin, Ohio, Kimberly Clark in Neena, Wis., Molnycke Health Care in Newtown, Pa., and Precept Medical Products, Inc., in Arden, N.C. Other materials suitable for use in surgical gowns 100 described herein will be obvious to those of ordinary skill in the art having the benefit of this disclosure.

The non-woven fabric can be a disposable material, and optionally can include and water resistant lining that prevents the passage of fluids through the body-covering portion 101. In another embodiment, the surgical gown 100 is configured to be reusable after an appropriate cleaning and sterilization process has been applied. In one embodiment, the length of the surgical gown 100 is configured to run from a wearer's shoulder to below their knee.

A first sleeve 102 and a second sleeve 103 can be included. Where so, the first sleeve 102 and second sleeve 103 extend distally from the body-covering portion 101. The optional first sleeve 102 and the second sleeve 103 are configured to receive wearer's arms when the surgical gown 100 is donned. In the illustrated embodiment of FIG. 1, the first sleeve 102 and second sleeve 103 are illustrated as long sleeves, and terminate in a first cuff 104 and a second cuff 105, respectively. However, it will be clear to those of ordinary skill in the art having the benefit of disclosure that embodiments of the invention are not so limited. Surgical gowns in accordance with embodiments of the invention may equally be configured with short sleeves or no sleeves has a particular application may warrant.

As shown in FIG. 1, surgical gown 100 may optionally include pockets 106,107 or other surface features. A front portion 108 of the surgical gown 100 is configured to be placed against the front of the torso. The body-covering portion 101 then wraps around and terminates at a body opening 109 having a first side 110 and a second side 111. In the illustrative embodiment of FIG. 1, the body opening 109 is configured as a slit that runs the length of the body-covering portion 101, up the back of the surgical gown 100, terminating at a neck opening 112. The first side 110 and second side 111 of the body opening 109 are configured to permit the wearer to don the surgical gown 100 by wrapping the first side 110 and second side 111 about the wearer's torso.

In one embodiment, one of the first side 110 or the second side 111 includes a coupling device, e.g., a belt or other cinching device, which extends therefrom. These coupling devices are sometimes referred to a "securement straps," in that they word to keep the surgical gown 100 securely on the wearer's torso. The coupling device is configured to wrap about the wearer and span the body opening 104. In one embodiment, the coupling device includes an adhesive that is configured to attach to the non-woven material on the other side of the body opening. The coupling device can be configured as a tie, strap, hook-and-loop type fastener, or other closure mechanism. Further, the closure device can include a plurality of outer and/or inner ties for securing the surgical gown 100 about a wearer's torso.

Where a coupling device is included, once the wearer dons the surgical gown, the coupling device can be wrapped about the torso, such as about the wearer's waist, and in one embodiment, adhesively affixed to the other side. When the wearer wishes to remove the surgical gown 100, this can be accomplished in a variety of ways. In a first embodiment, the coupling device may simply be torn. In another embodiment, where and adhesive is used, a selectively detachable adhesive can be chosen that forms a non-permanent bond with the non-woven material such that the wearer can selectively detach the coupling device from the body-covering portion 101. In such an embodiment, when the wearer wants to remove the surgical gown 100, the wearer simply pulls the coupling device from the opposite side of the body opening 109 to release the adhesive bond.

In the illustrative embodiment of FIG. 1, the coupling device is configured as a plurality of ties 114,115,116,117. The ties 114,115,116,117 of this illustrative embodiment include outer ties 114,115,116 and inner tie 117. The outer ties 114,115,116 and inner tie 117 can be used for fastening the body-covering portion 101 around the torso when the wearer dons the surgical gown 100. Further, the outer ties 114,115,116 and inner tie 117 can be used to keep the first side 110 and second side 111 closed. For example, the ties 114,115,116,117 may be attached to the surgical gown 100 such that, when in use, the first side 110 overlaps the second side 111 or vice versa. In other configurations, the ties 114,115,116,117 can be attached to the surgical gown 100 such that the first side 110 and second side 111 do not overlap, but rather meet to provide adequate closure. The ties 114,115,116,117 may be made of the same material as the body-covering portion 101, or may be made from other suitable materials. It is well to note that the number and placement of ties 114,115,116,117 may vary.

Embodiments of the surgical gown 100 can be manufactured in a variety of ways. For instance, in one embodiment the body-covering portion 101 is a single piece of material. In other embodiments, the body-covering portion 101 is configured as separate sections that are stitched, ultrasonically sealed, or otherwise attached together. Where included, the sleeves 102,103 may be attached to the body-covering portion 101 by stitching, ultrasonic sealing, or other appropriate method of attachment. Similarly, the ties 114,115,116, 117 may be integrated with the body-covering portion 101, or may be attached using glue, tape, stitching, ultrasonic sealing, or other appropriate attachment method.

In the illustrative embodiment of FIG. 1, a surgery procedure verification card 120 is removably attached to the surgical gown 100. In another embodiment, the surgery procedure verification card 120 can be removably attached to the coupling devices or securement straps. For example, the surgery procedure verification card 120 may be coupled to tie 116 or tie 115 in one embodiment.

Where the surgery procedure verification card 120 is coupled to the securement straps, the surgery procedure verification card 120 can be configured as a "pass card." A "pass card" is a card that is large enough to be passed between a sterile team and a non-sterile team. This is most easily explained way of example: When a medical team is preparing for surgery, often the team will divide into two parts. One part will initially be the "sterile team," while the other part is initially the "non-sterile" team. The surgeon will be on the sterile team. Using the surgeon as an example, once the surgeon has sterilized herself, she dons the surgical gown 100. To remain sterile, she is unable to place her arms behind her back or touch any member of the non-sterile team.

For such a situation, the surgery procedure verification card 120 is coupled to the securement devices, which are referred to as "pass ties." Further, the surgery procedure verification card 120 is configured to be large enough such that the sterile team can touch one portion and the non-sterile team can touch another portion that is spaced away from the first portion. In such a configuration, the surgeon will grasp the sterile portion of the surgery procedure verification card 120, which is coupled to a securement device, and will hand it to the non-sterile team, which grasps a portion of the surgery procedure verification card 120 that the surgeon has not touched. The non-sterile team then holds the card such that it pulls the securement device away from the surgeon. The surgeon then spins, wrapping themselves in the securement device attached to the surgery procedure verification card 120, i.e., the "pass card" in this illustration. Once wrapped, the non-sterile team pulls and detaches the pass card from the securement straps so the surgeon can effectively tie their gown at waist level, leaving the pass card with the circulating nurse which is part of the non-sterile team Accordingly, the "pass card" permits a sterile team member to don the surgical gown 100 without compromising their sterile field.

As will be described in more detail below, in one embodiment the surgery procedure verification card 120 is configured to facilitate the start of a surgical procedure in accordance with a predetermined pre-surgery procedure. In another embodiment, the surgery procedure verification card 120 is configured to facilitate a verification of completion of the predetermined pre-surgery procedure prior to the initiation of surgery. Said differently, the surgery procedure verification card 120 facilitates a time out procedure prior to a surgeon making the first incision.

In one embodiment, a neck binding 113 is coupled to the body-covering portion 101 of the surgical gown 100. The neck binding 113 can be attached using glue, tape, stitching, ultrasonic sealing, or other appropriate attaching method. In one embodiment, the neck binding 113 includes a color-coding that indicates that the surgery procedure verification card 120 is attached. For example, in one embodiment the body covering portion 101 and the neck binding 113 can be different colors when a surgery procedure verification card 120 is attached. In one embodiment, the body-covering portion 101 may be blue, while the neck binding 113 is yellow, green, purple, or red. In another embodiment, the neck binding 113 is stitched to the body-covering portion 101 and therefore includes one or more visible stitched seams 121. To provide color-coding, the stitched seam 121 of the neck binding 113 can be colored differently from the neck binding 113, the body-covering portion 101, or both. For instance, the neck binding 113 may be navy blue while the stitched seam 121 is white or yellow, and so forth. The color-coded neck binding 113 provides an easy visual indicator with which a nurse or other healthcare services provider may readily identify which gown is the surgeon's gown, and further which gown has the surgery procedure verification card 120 attached thereto. This can be helpful when the surgery gown 100 is packaged with one or more surgical procedure gowns.

In one embodiment, where sleeves 102,103 are included, the corresponding cuffs 104,105 can also be optionally color-coded. In the illustrative embodiment of FIG. 2, cuff 105 is shown as color-coded. For example, the cuffs 104,105 can have the same color-coding as the stitched seam 121. Alternatively, either of the stitched seam 121 or the neck binding 113 can have a color indicating a first property or feature of the surgical gown 100, while the cuffs 104,105 can have a color indicating an additional property or feature of the surgical gown.

In one embodiment, the neck binding 113 includes dual color-coding. For instance, the neck binding 113 itself can be a first color, indicative of a first property, while the stitched seam 121 is a second color, indicative of a second property. (The stitched seam 121 is illustrative only, as a painted, dyed, tattooed, screened, or other demarcation can be used in place of the stitched seam 121 to provide color-coating properties.)

As noted above, in one embodiment the stitched seam 121 is color-coded to indicate the presence of a removably attached surgery procedure verification card 120. In one embodiment, the color of the neck binding 113 can also be color-coded to indicate a barrier protection level corresponding to the surgical gown 100. The barrier protection level designates the ability of the town to protect against the penetration of fluids and infectious materials. Barrier efficacy is recognized by those of ordinary skill in the art as important to helping protect patients and health care personnel, and is also important in protecting against the transmission of infectious vectors. The Occupational Safety and Health Administration (OSHA) has adopted regulations limiting the occupational exposure to blood-borne pathogens. See, e.g., 29 CFR 1019, 1030, (July 2003). Further, the Centers for Disease Control and Prevention has published its "Guidelines for the Prevention of Surgical Site Infection," which also sets forth recommendations that drapes and gowns be impermeable to liquids and viruses.

One organization that has established a standard for barrier protection levels is the Association for the Advancement of Medical Instrumentation (AAMI). The current standard is set forth in "Liquid Barrier Performance and Classification of Protective Apparel and Drapes Intended for Use in Health Care Facilities." AAMI PB70:2003. This standard helps to preserve the sterile field and protect health care personnel during surgery from exposure to blood, bodily fluids, and other potential infections materials. The standard further establishes a system and classification of minimum requirements for protective apparel used in health care facilities based upon liquid-barrier performance.

The present AAMI standard for liquid-barrier performance is set forth in the following table:

TABLE 1

AAMI Barrier Protection Levels

| AAMI LEVEL | TEST | RESULT |
| --- | --- | --- |
| 1 | AATCC 42: 2000 | ≤4.5 g |
| 2 | AATCC 42: 200 | ≤1.0 g |
|   | AATCC 127: 1998 | ≥20 cm |
| 3 | AATCC 42: 2000 | ≤1.0 g |
|   | AATCC 127: 1998 | ≥50 cm |
| 4 | Gowns: ATSM F1671: 2003 | Pass |
|   | Drapes: ATSM F1670: 2003 | Pass |

As shown in TABLE 1, the AAMI uses two tests developed by the American Association of Textile Colorists and Chemists (AATCC). AATCC 42 measures a materials water resistance by impact penetration. The material is held at a 45-degree angle while a fixed amount of water is sprayed. A blotter is affixed under the material and is weighed both before and after the spray. According to the AAMI, the material qualifies as Level 1 if the blotter's weight-gain is no more than 4.5 grams.

For Level 2, two tests must be satisfied. The additional test is AATCC 127, which measures a material's resistance to water penetration under hydrostatic pressure. Under this test, a sample of the material is placed horizontally on the bottom of a metered glass cylinder. Hydrostatic pressure is increasingly applied. To be acceptable for AAMI Level 2, not only should the blotter's weight-gain be less than 1 gram, but also the material must be able to resist penetration when the water level reaches a depth of 20 cm. These examples will explain the requirements for Level 3 as well.

For AAMI Level 4, two tests developed by the American Society of Testing Materials (ATSM) are used. F1670 is for liquid penetration, and F1671 is for viral penetration. For Level 4, both tests must be passed.

While one embodiment of color-coding described herein is with reference to the AAMI tests, it will be clear to those of ordinary skill in the art having the benefit of this disclosure that embodiments of the invention are not so limited. It is contemplated that other barrier protection level standards may be substituted for the AAMI standards without departing from the spirit and scope of the claims. The AAMI standards are illustrative only. Such other barrier protection level standards include standards that have been developed or will be developed by the AAMI or other industry groups or standards boards.

As noted above, in one embodiment the color-coding of the neck binding 113 can be used to identify the barrier protection level associated with the surgical gown 100. In one embodiment, the color-coding can correspond to barrier levels designated by the AAMI in standard AAMI PB70: 2003. For example, a surgical gown 100 having a Level 1 barrier protection may have a neck binding 113 that is a first color, such as yellow. A surgical gown 100 having a Level 2 barrier protection may have a neck binding 113 that is a second color, such as green. A surgical gown 100 having a Level 3 barrier protection may have a neck binding 113 that is a third color, such as purple. A surgical gown having a Level 4 barrier protection may have a neck binding that is a fourth color, such as dark blue. Note that while the neck binding 113 is being described as indicating barrier protection, with the stitched seam 121 indicating the presence of the surgery procedure verification card 120, the reverse could be true, with the stitched seam 121 indicating barrier protection and the neck binding 113 indicating the presence of the surgery procedure verification card 120. Other color-coding schemes will be readily apparent to those of ordinary skill in the art having the benefit of this disclosure. For example, the neck binding 113 can include a pattern, design, text, characters, graphics, or other indicia in combination with, or in lieu of, the color-coding techniques described herein. Further, the color-coding could be applied to other portions of the surgical gown 100 in addition to, or in lieu of, the neck binding 113.

Figure 2:
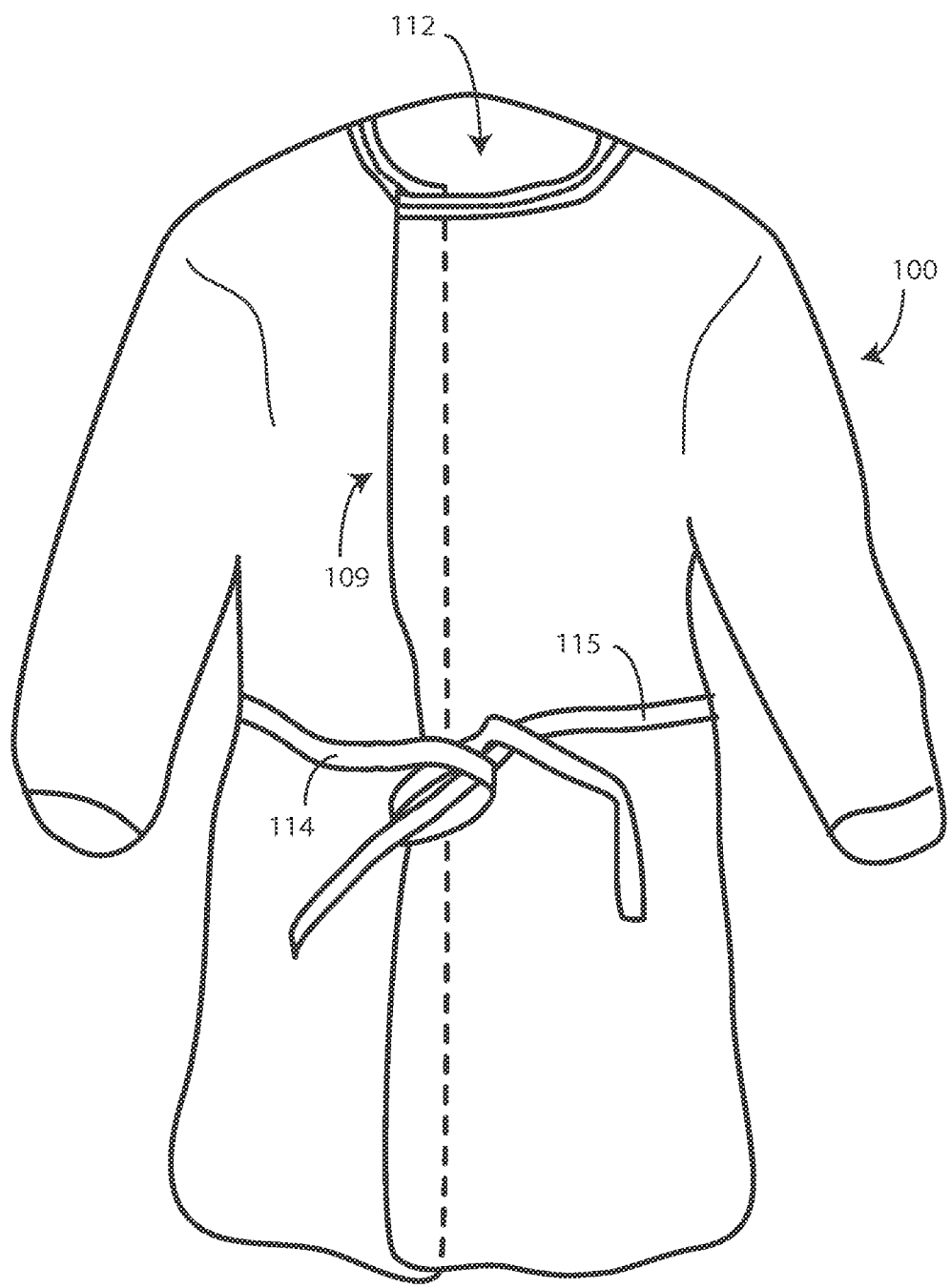
FIG. 2 illustrates a rear view of one embodiment of a medical gown configured in accordance with one or more embodiments of the invention.

Turning now to FIG. 2, illustrated therein is a rear view of a surgical gown 100 configured in accordance with embodiments of the invention. From this view, the body opening 109 and neck opening 112 can more readily be seen. The surgical gown 100 of FIG. 1 is illustrated once tabs 114,115 have been bound together to close the body opening 109. In this illustrative embodiment, one tab 114 is shown as being disposed approximately waist-high so as to span the body opening 109 about the waist of the wearer. It will be clear to those of ordinary skill in the art having the benefit of this disclosure, however, other configurations are possible. For example, the tabs may be disposed at other locations along the body opening 109, such as shoulder-high or mid-back.

Figure 3:
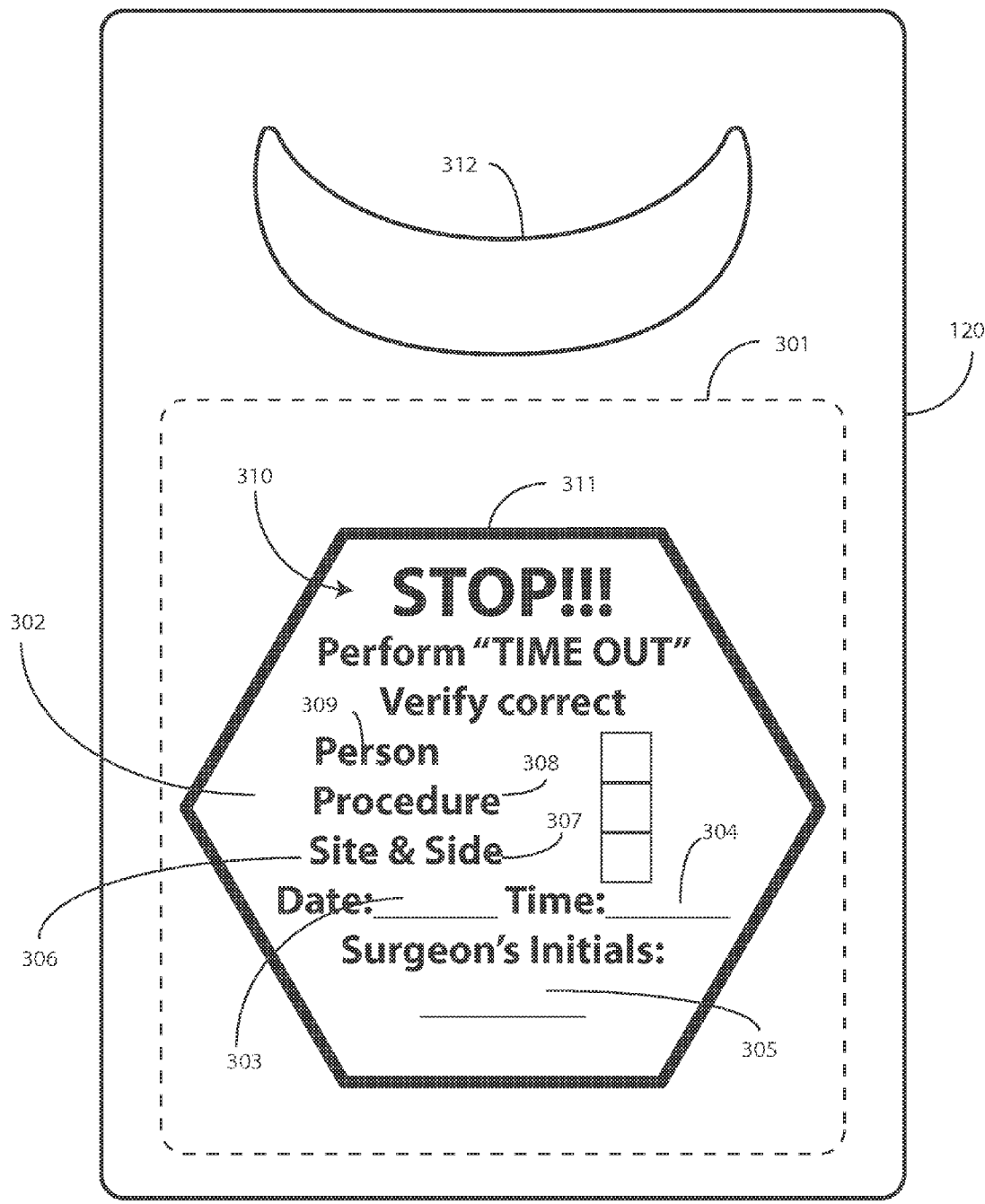
FIG. 3 illustrates a front view of one surgery procedure verification card configured in accordance with embodiments of the invention.

Turning now to FIG. 3, illustrated therein is one embodiment of a surgery procedure verification card 120 configured in accordance with embodiments of the invention. As will be described below, the surgery procedure verification card 120 of FIG. 3 is configured to facilitate verification of completion of the predetermined procedure, which in one embodiment is a time out procedure. By attaching the surgery procedure verification card 120 to a surgeon's surgical gown, the card works to prevent the surgeon from performing surgery on the wrong patient, as well as preventing them from performing the wrong surgical procedure, at the wrong surgical site or side of the patient. In effect, the surgeon is forced to perform a pause or time out before the surgical procedure begins because the surgery procedure verification card 120 is physically attached to her gown. At a minimum, the surgeon must at least consider the time out procedure. This pause allows the surgical staff to confirm the correct surgical patient, surgical procedure, and surgical site and side.

The illustrative surgery procedure verification card 120 of FIG. 3 includes an instruction 310 to "STOP!! Perform 'TIME OUT' Verify Correct Person, Procedure, Site & Side." In accordance therewith, the surgical staff must stop, verify the correct person (by, for example, confirming the patient's name and date of birth), verify the correct procedure, verify the correct site and verify the correct side before the surgical procedure can begin. By prominently displaying the predetermined instruction 310 on the surgery procedure verification card 120, the staff is more easily directed not to overlook the important steps that should be performed before the surgery begins. These steps will reduce the occurrences of "wrong patient," "wrong procedure," "wrong site" and "wrong side" surgeries. Surgical staff, hospitals and patients will benefit by the reduction or elimination of such occurrences.

The instruction 310 may include any shape that may be positioned on the indicator 301, such as the octagon 311 illustratively shown in FIG. 3. The octagon 311 may be used to resemble a stop sign and will caution the surgical staff to pause before proceeding. Other shapes may include a circle, a square, a diamond, a triangle, a heart, a hexagon, a rectangle, an oval, or a pentagon, and/or any other shapes that would be suitable for positioning on the indicator 301. The surgery procedure verification card 120 can be color-coded. For example, the octagon 311 may also include a specific color, such as red, to draw the attention of the surgical staff to remind them of the need to complete the predetermined verification procedure.

The illustrative surgery procedure verification card 120 of FIG. 3 includes an indicator 301 upon which confirmation of completion of the predetermined procedure can be recorded. In one embodiment, the indicator 301 is configured with a listing 302 of conditions to be completed or verified prior to the start of the surgical procedure. In the illustrative embodiment of FIG. 3, the conditions include: confirming a correct surgical site 306; confirming a correct surgical procedure 308; confirming a correct patient 309; and confirming a correct patient portion 307 for the surgical procedure.

In one embodiment, the indicator 301 is configured to accept writing and markings from writing instruments such as pens and markers such that a healthcare provider can mark off each of the conditions as they are completed. Accordingly, the surgical staff may indicate that each part of the time out procedure has been conducted, for example by marking or checking off a box corresponding to each step. Additionally, in one embodiment there are placeholders 303,304,305 for denoting the date, time, and initials of the surgeon to verify the completion of each step or condition.

In one embodiment, the indicator 301 is attached to the surgery procedure verification card 120. For example, the listing 302 can be a stamp, an embossment, a tattoo, or an ink or screen-printed article that is disposed on a major face of the surgery procedure verification card 120. In another embodiment, the indicator 301 is configured to be selectively removable from the surgery procedure verification card 120. For example, the indicator 301 can be configured as a label, attached paper, sticker, decal, or other removable item. The indicator 301 may be attachable to the surgery procedure verification card 120 and may be removed therefrom upon completion of the predetermined verification procedure. For example, the indicator 301 may have an adhesive material on one side of the decal, sticker, stamp, etc. that allows it to be removably attached to the surgery procedure verification card 120. In either embodiment, the indicator 301 can be configured for placement in a patients medical records, as will be described with reference to FIG. 7

It is to be noted that the examples described herein and shown in FIG. 3 include four different elements to be verified, i.e., the person, the procedure, the site and the side. However, it will be clear to those of ordinary skill in the art having the benefit of this disclosure that the predetermined verification procedure may contain only one of these elements, a combination of these elements, or additional elements that may be different from the elements shown in FIG. 3. For example, the predetermined verification procedure may also include verifying other elements, in addition to or as an alternative to those described above, such as verifying the correct position of the patient, the correct radiograph data (if needed), the availability of special equipment, implants and other requirements, any allergies the patient may have, any pre-operative antibiotics or medications that the patient is taking, any blood products that may be needed for transfusions prior to the surgical procedure or intraoperatively, the location of the family while at the hospital for communication purposes, and other elements that are relevant in a surgical setting.

The surgery procedure verification card 120 may be coupled to the surgical gown (100) in a variety of ways. In the illustrative embodiment of FIG. 3, the surgery procedure verification card 120 defines an aperture through which gown material may be pulled. Any number of other attachment devices can be substituted without departing from the spirit and scope of the claims. For example, the surgery procedure verification card 120 may be adhesively attached to the surgical gown (100), sewn to the surgical gown (100), attached by way of a perforation in the surgery procedure verification card 120, frictionally attached, press-fit, pinned, snapped, and so forth. Garment-tag attachment devices are a well-developed art. Accordingly, the voluminous number of possible alternatives will not be described here in the interest of brevity.

As discussed above, in one embodiment, the surgery procedure verification card 120 facilitates prevention of the start of a surgical procedure until the surgical staff performs the required procedure to verify the correct patient, the correct surgical procedure, the correct site and the correct side. Once all of these elements have been verified, the surgeon or other surgical staff member may remove the surgery procedure verification card 120 from the surgical gown (100) and may begin the surgical procedure. One example of a predetermined verification procedure suitable for use with the surgery procedure verification card 120 for preventing surgical errors is that developed by The Joint Commission's 2008 National Patient Safety Goal's "Universal Protocol." According to the Universal Protocol, a time out is conducted in the location where the surgical procedure will be performed, just before the procedure is to be started. The time out may involve the entire surgical team, who must use active communication, and may be briefly documented, such as by using a checklist. The Universal Protocol includes, at the least, verification of the correct patient identity, the correct side and site, an agreement on the procedure to be done, the correct patient position and the availability of correct implants and any special equipment or special requirements.

Figure 4:
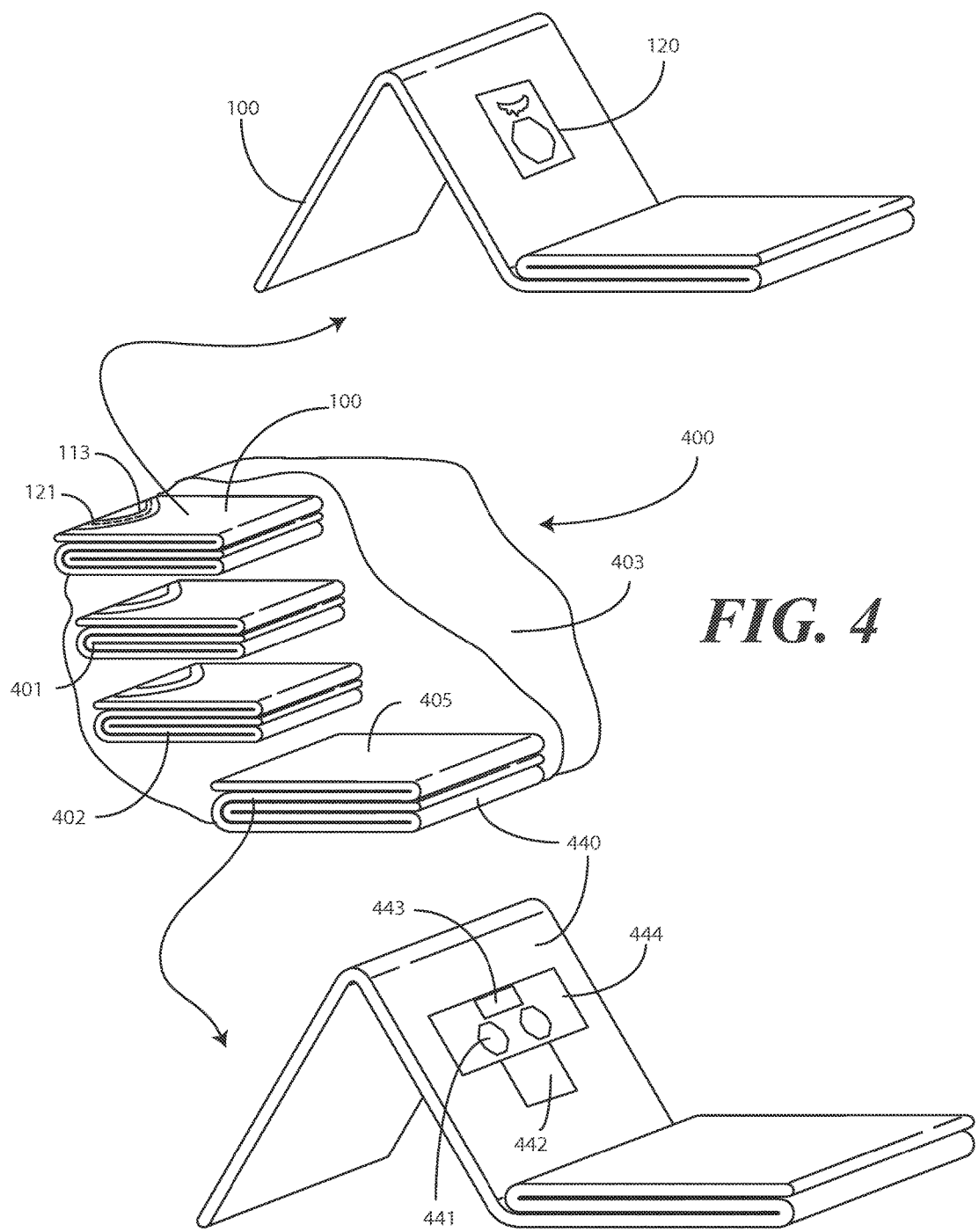
FIG. 4 illustrates one or more packaging embodiments suitable for medical gowns and drapes configured in accordance with embodiments of the invention.

Turning now to FIG. 4, illustrated therein is one embodiment of a surgical pack 400 that includes a surgical gown 100 configured in accordance with embodiments of the invention. A manufacturer having the benefit of this disclosure may package the surgical gown 100 with one or more surgical procedure gowns 401,402 in a sterile packaging 403 for sale and delivery to a hospital or other healthcare services provider. In one embodiment, the surgical gown 100 is configured to be worn by the surgeon, while the one or more surgical procedure gowns 401,402 are configured to be worn by the surgical support staff.

In one embodiment, only one of the garments in the surgical pack 400 includes the surgery procedure verification card 120. As shown in FIG. 4, it can be the case that the surgery procedure verification card 120 is not visible until after the surgical gown 100 is unfolded. To make identification prior to unfolding, or in some cases prior to unwrapping, in one embodiment only the surgical gown 100 includes the color-coding indicative of the surgery procedure verification card 120 being attached thereto. For instance, the neck binding 113 of the surgical gown 100 can include the stitched seam 121 described above, while the neck bindings 404,405 of the one or more surgical procedure gowns 401,402 include no card-related color-coding. It is contemplated, however, that any or all of the neck bindings 113,404,405 can include color-coding indicative of barrier level as described above.

In addition to the gowns, in one embodiment the surgical pack 400 further includes a surgical drape 440 as described in commonly assigned U.S. application Ser. No. 12/008,818, filed Jan. 14, 2008, which was incorporated by reference above. In one embodiment, the surgical drape 440 includes a base sheet having a top surface and a bottom surface. The surgical drape 440 may include panels 441,442. Panel 441 may be adapted for use as a reinforcement panel that absorbs blood and fluid from a surgical site. Panel 442 may be adapted for use as an anti-skid mat to prevent instruments from sliding on the surgical drape 440.

The surgical drape 440 can also include an opening or fenestration 443 for positioning over a surgical site. The fenestration 443 may be centrally located in the surgical drape 440 or may be positioned at other non-central locations in the surgical drape 440. The illustrative fenestration 443 of FIG. 4 is rectangular, but may include any other shapes that would be suitable for positioning over a surgical site.

In one embodiment, positioned across the fenestration 443 is a barrier 444 for preventing the start of a surgical procedure. The barrier 444 works similarly to the surgical procedure verification card 120, in that it requires or facilitates completion of a predetermined process prior to the operation beginning. The barrier 444 may include a strip of material that is attached to the surgical drape 440 along a portion of the periphery of the fenestration 443. The barrier 444 may be made of any type of material that may be attached to a surgical drape 440, such as paper, cloth, polymeric materials, wax-covered paper, combinations thereof and any other material that would be suitable for attaching to the surgical drape 440.

In one embodiment, the barrier 444 may be attached to the bottom surface of the surgical drape 440 via an adhesive material located around the periphery of the fenestration 20. The barrier 444 may be attached to the surgical drape 440 at two or more locations such that the barrier 444 is attached on one side of the fenestration 443 at a first location and is also attached on another side of the fenestration 443 at a second location directly opposite the first location. It is contemplated that the barrier 444 could be attached at other locations around the periphery of the fenestration 443. In addition to adhesives, the barrier 444 may be attached to the surgical drape 440 using hook and loop fasteners, e.g., Velcro®, string, loops, ties and other materials that would be suitable for attaching the barrier 444. In some embodiments, attached to the adhesive material are one or more attachment strips that are removed when the surgical drape 440 is positioned on the patient. In one embodiment, the barrier 444 is positioned across the fenestration 443 to prevent the start of a surgical procedure until a predetermined verification procedure is completed.

When using the surgical pack 400, a circulation nurse will open the packaging 403 and identify the surgical gown 100 from the color-coding that is indicative of the surgery procedure verification card 120 being attached thereto. The surgeon will don the surgical gown 100 as shown in FIG. 6, while the staff dons the one or more surgical procedure gowns 401,402. The surgical drape 440 will the be placed over at least a part of a patient, as shown in FIG. 5.

Figure 5:
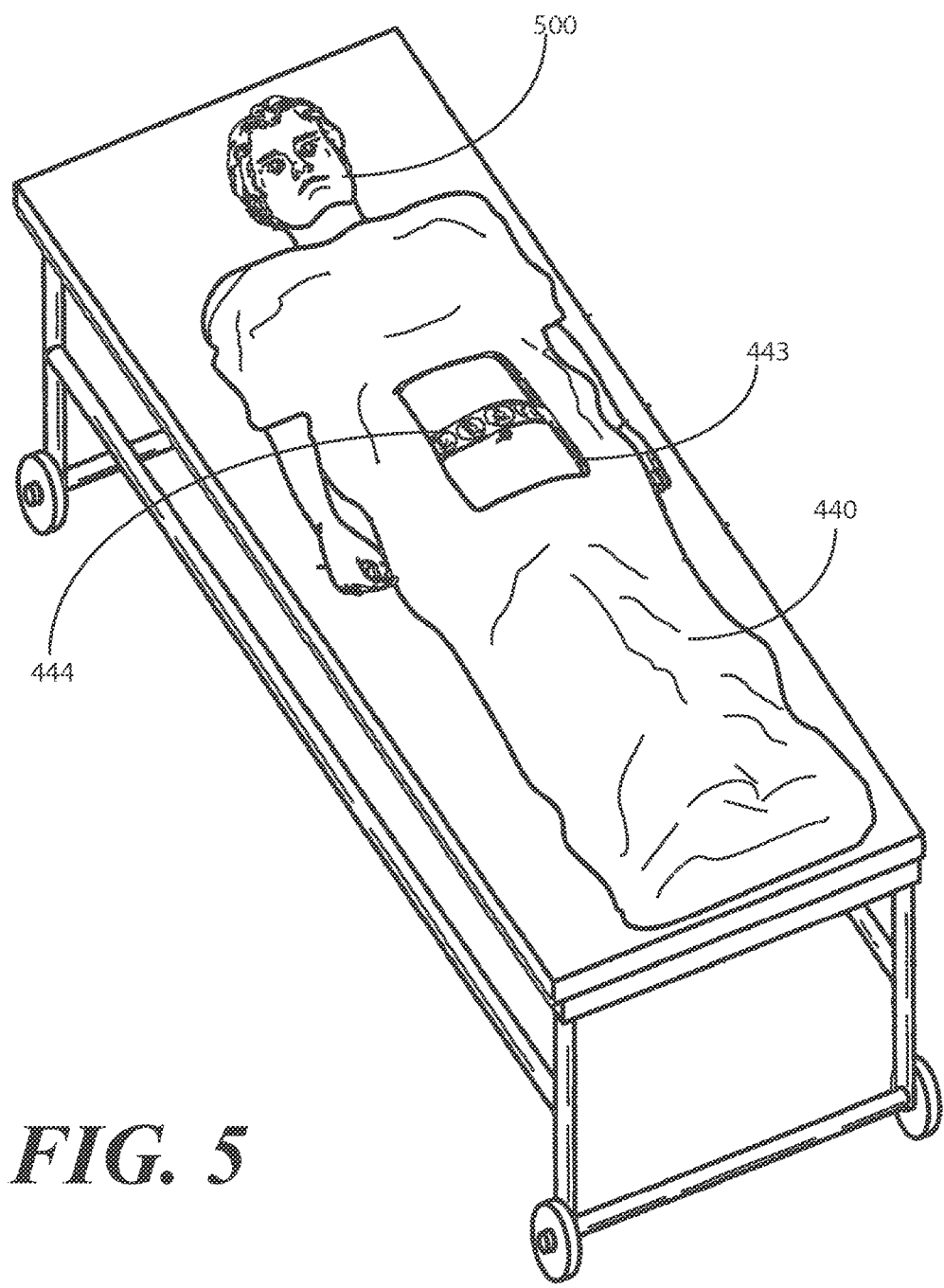
FIGS. 5 and 6 illustrate one or more applications for medical equipment employing procedure verification cards in accordance with one or more embodiments of the invention.
Figure 6:
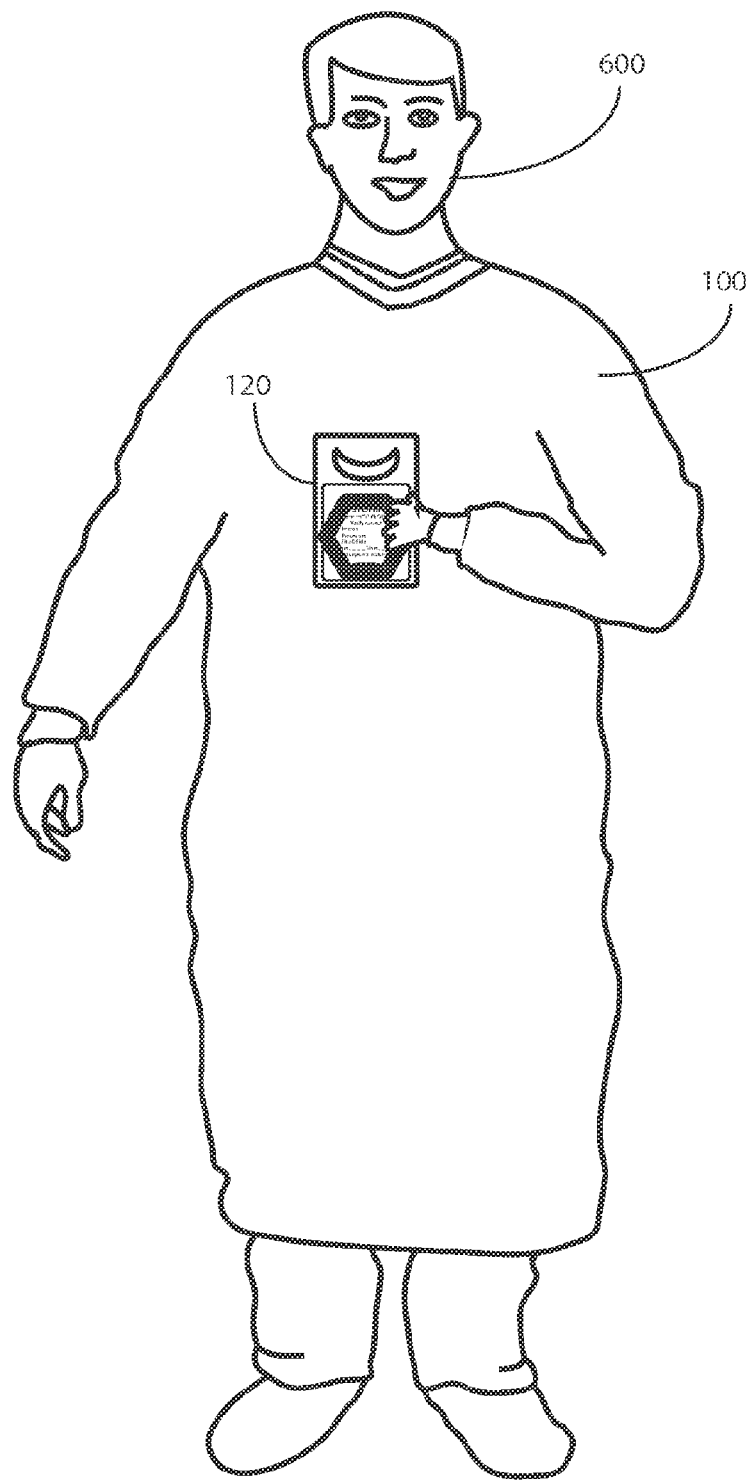

Turning now to FIG. 5, illustrated therein is a patient 500 once the surgical drape 440 is in place. As shown, the barrier 444 is disposed across the fenestration 443. Once the predetermined verification procedure is completed, and the barrier 444 can be removed by a member of the surgical staff. In one embodiment, the barrier 444 may be removed from the surgical drape 440 by the surgeon or other surgical staff member by tearing the barrier 444 at one or more perforations.

Turning now to FIG. 6, illustrated therein is a surgeon 600 having donned the surgical gown 100. Once the predetermined verification procedure is completed, as shown with reference to FIG. 7, the surgery procedure verification card 120 can be removed. In one embodiment, either the surgery procedure verification card 120 or an indicator (301) detachable therefrom can be inserted in the medical records of the patient (500).

Figure 7:
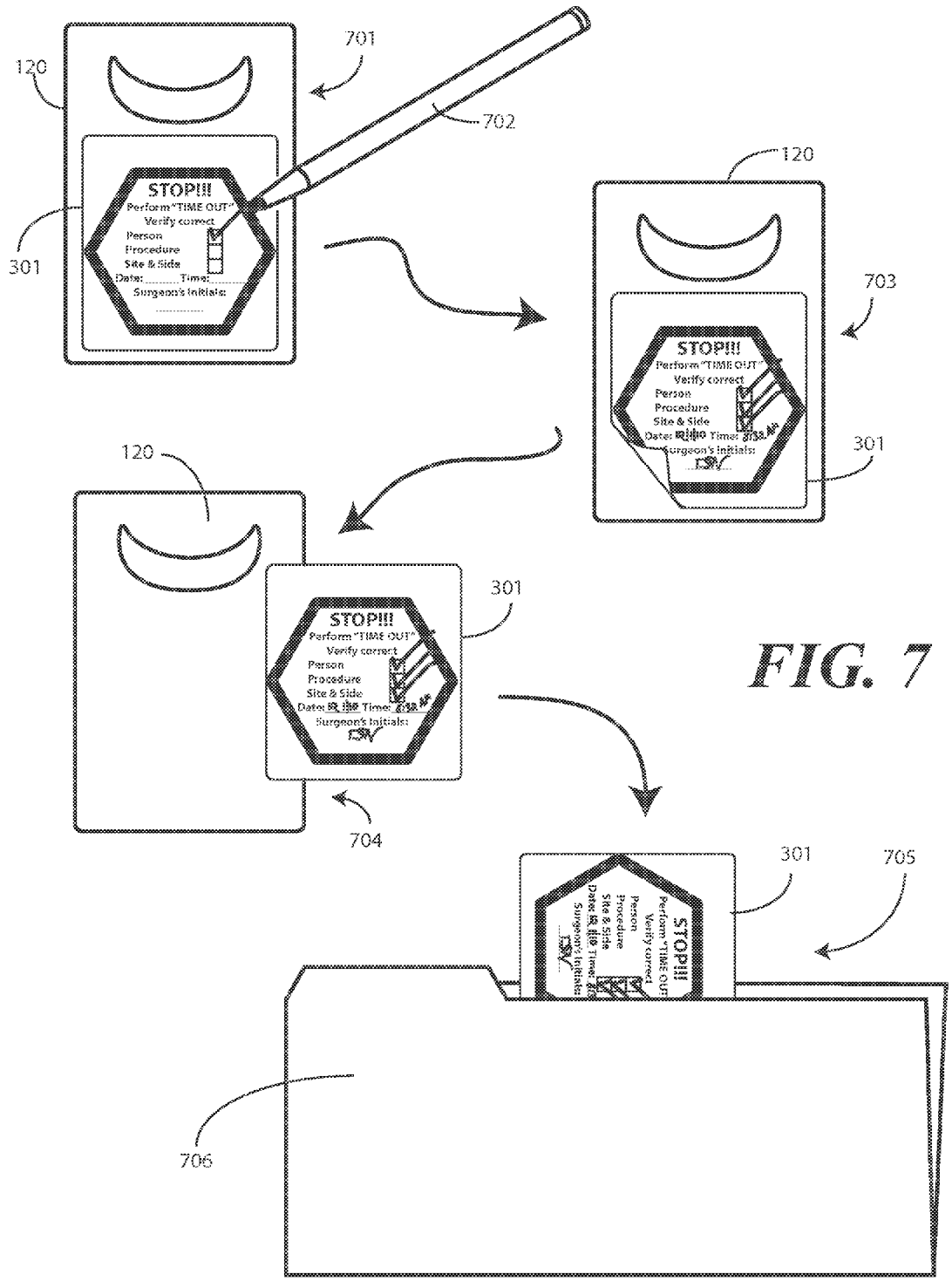
FIG. 7 illustrates one method of using embodiments of procedure verification cards configured in accordance with embodiments of the invention.

Turning now to FIG. 7, illustrated therein are the graphical steps of verifying and documenting that the predetermined verification procedure has been completed using one embodiment of a surgery procedure verification card 120 in accordance with one or more embodiments of the invention. In the illustrative method of FIG. 7, the surgery procedure verification card 120 is configured with a detachable indicator 301.

At step 701, after the surgery procedure verification card 120 has been detached from the surgical gown (100) as was shown in FIG. 6, a healthcare services provider verifies compliance with the predetermined procedure, which in one embodiment is a time out procedure. This verification can be recorded on the indicator 301. At step 701, the verification is being recorded by checking one or more boxes with a pen 702 or marker.

At step 703, the indicator can be removed from the surgery procedure verification card 120. In this illustrative embodiment, this is accomplished by lifting a corner of the indicator and pulling it across a major face of the surgery procedure verification card 120. The result is an indicator 301 that is separate from the surgery procedure verification card 120, as shown at step 704. The healthcare services provider can then place the indicator 301 in the patient's medical record 706, as shown at step 705. Had the indicator 301 not been detachable from the surgery procedure verification card, another option would have been to simply place the entire surgery procedure verification card 120 in the patient's medical record 706.

Figure 8:
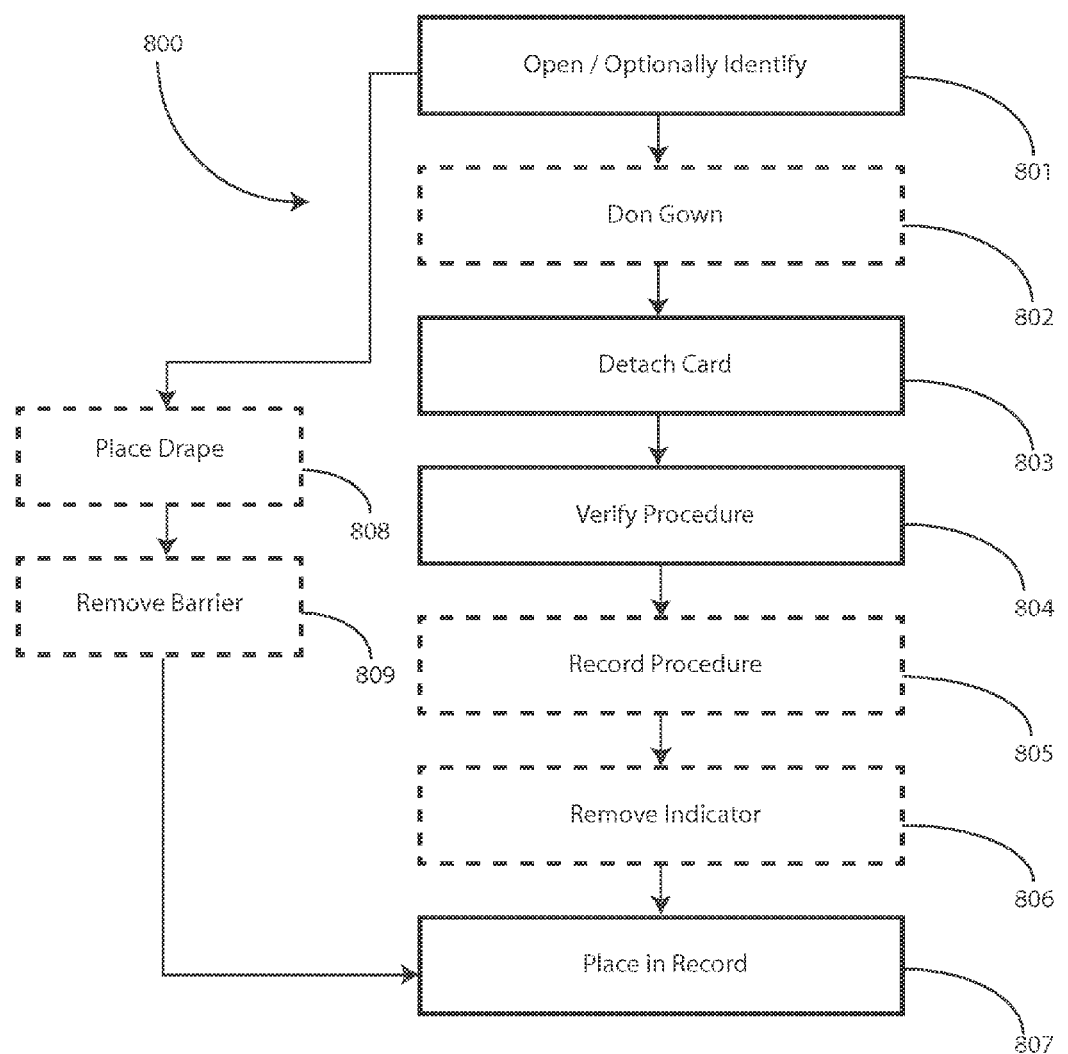
FIGS. 8 and 9 illustrates methods of making and using embodiments of medical gowns and drapes described herein.

Turning now to FIG. 8, illustrated therein is a flow chart depicting a method 800 of using a surgical gown 100 in accordance with one or more embodiments of the invention. It should be understood that the method 800 of FIG. 8 is illustrative only, as other methods could be used as well. Further, most of the steps shown in FIG. 8 have been described above, so will only be briefly described here.

Where the surgical gown (100) was included in a surgical pack (400) the packaging can be opened at step 801. Step 801 can optionally include the step of identifying the surgical gown (100) from a color-coding indicative of the surgery procedure verification card (120) being attached thereto.

At step 802, the surgical gown (100) is applied to a surgeon. The surgeon can don the gown with a surgery procedure verification card (120) attached thereto, and can detach the surgery procedure verification card (120) from the surgical gown (100) at step 803. Alternatively, step 803 can occur before step 802, with step 802 forming the final step of the method 800 of FIG. 8.

At step 804, compliance with the predetermined procedure, using the surgery procedure verification card (120), can be verified prior to beginning a surgical procedure. At step 805, this verification can be recorded. Illustrative actions for completing steps 804 and 805 were shown and described with respect to FIG. 7 above. Where the indicator (301) is removable from the surgery procedure verification card (120), the indicator (301) can be removed at step 806. One embodiment of step 806 was illustratively shown in FIG. 7. At step 807, either the indicator (301) or the surgery procedure verification card (120) can be placed in a patient's medical record (706).

Parallel steps can be included where the surgical gown (100) is included in a surgical pack (400) that includes a surgical drape (440). For example, at step 808, the surgical drape (440) may be placed over at least a part of a patient (500). Where the surgical drape (440) comprises a fenestration (443) and a barrier (444) that is removably attached to the surgical drape (440), the barrier (444) can be removed at step 809 after compliance with the predetermined procedure is verified. As with the surgery procedure verification card (120), the barrier (444) or an indicator that is removably attached thereto can be placed in the patient's medical record (706) at step 807.

Figure 9:
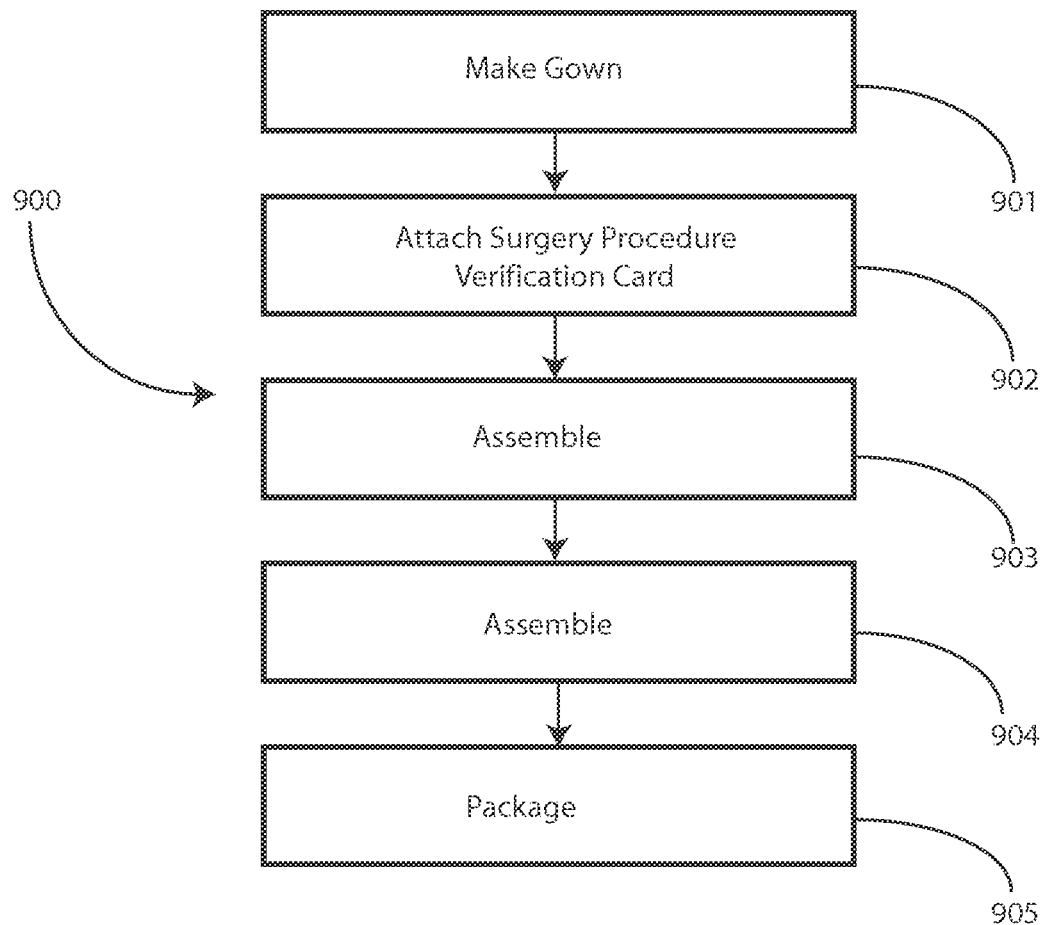

Turning now to FIG. 9, illustrated therein is one method of manufacturing a surgical gown (100) in accordance with embodiments of the invention. As the general manufacture of the gown itself was described above, the method 900 of FIG. 9 will begin with a completed gown and then focus on the subsequent steps, including the packaging and shipment steps. However, the general manufacture step 901 is included in the method 900 for illustration. Note that this step 901 can include color-coding the surgical gown (100), where the color-coding is indicative of either a barrier level or the fact that a removable surgery procedure verification card is attached to the surgical gown (100).

At step 902, a surgery procedure verification card (120) can be attached to the surgical gown (100). As noted above, in one embodiment the surgery procedure verification card (120) is attached so as to be removable by a user for facilitation of a start of a surgical procedure after a predetermined procedure is completed, and optionally documented.

At optional step 903, the surgical gown (100) can be assembled with one or more surgical procedure gowns (401,402). In one embodiment, the one or more surgical procedure gowns (401,402) are not color-coded and do not include surgery procedure verification cards attached thereto. At optional step 904, the surgical gown (100) can be assembled with a surgical drape (440) having a fenestration to be placed over a surgical site of a patient and a barrier, removably attached to the surgical drape (440) and adapted for placement over a portion of the fenestration. As described above, the barrier (444) can be configured to prevent the start of the surgical procedure until the predetermined procedure is completed.

At step 905, the assembly can be placed into packaging and sealed as a surgical pack (400). In one embodiment, the surgical pack (400) is sterile and the packaging is configured to keep the contents sterile until opened and ready for use.

A gown comprising a body-covering portion and a procedure verification card, removably attached to the gown, and configured to facilitate a start of a medical procedure after completion of a predetermined procedure presented on the procedure verification card, wherein the procedure verification card is coupled to the gown by one of an aperture through which gown material may be pulled, adhesive attachment, sewing, perforation, frictional attachment, press-fitting, pinning, snapping, or combinations thereof.

In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A gown comprising:
   a body-covering portion; and
   a procedure verification card, removably attached to the gown, and comprising a predetermined procedure;
   the gown comprising a color-coding indicating that the procedure verification card is attached to the gown;
   the gown a surgeon's gown and packaged with one or more medical procedure gowns, only the surgeon's gown comprises the color-coding.

2. The gown of claim 1, the gown comprising a neck binding coupled to the body-covering portion, the neck binding comprising the color-coding.

3. The gown of claim 1, wherein at least one medical procedure gown of the one or more medical procedure gowns comprises another body-covering portion.

4. The gown of claim 3, further comprising one or more additional procedure verification cards.

5. The gown of claim 4, at least one procedure verification card of the one or more additional procedure verification cards is removably attached to the another body-covering portion.

6. The gown of claim 4, the at least one procedure verification card comprising an indicator.

7. The gown of claim 6, the indicator removable from the at least one procedure verification card.

8. The gown of claim 6, the indicator comprising an instruction of a predetermined procedure.

9. The gown of claim 8, the predetermined procedure comprising taking a time out to verify a correct patient.

10. The gown of claim 8, the predetermined procedure comprising taking a time out to verify a correct procedure.

11. The gown of claim 8, the predetermined procedure comprising taking a time out to verify a correct side of a patient for a surgical procedure.

12. The gown of claim 6, the indicator comprising one or more of a label, a sticker, a decal, a stamp, an embossment, a tattoo, or an ink or screen-printed article.

13. The gown of claim 12, the predetermined procedure comprising a listing of completion conditions prior to the start of a medical procedure.

14. The gown of claim 13, the listing of conditions comprises one or more of:
   confirming a correct site;
   confirming a correct medical procedure;
   confirming a correct patient; and
   confirming a correct patient portion for the correct medical procedure.

15. The gown of claim 6, wherein the another color-coding comprises a stitched seam coupling the neck binding to the another body-covering portion.

16. The gown of claim 15, wherein the stitched seam and the neck binding are different colors.

17. The gown of claim 4, the at least one procedure verification card comprising a verification of completion of a predetermined procedure.

18. The gown of claim 4, at least one procedure verification card of the one or more procedure verification cards comprising a stop sign symbol.

19. The gown of claim 4, at least one procedure verification card of the one or more procedure verification cards comprising one of "STOP" or "S.T.O.P" printed thereon.

20. The gown of claim 4, at least one procedure verification card of the one or more procedure verification cards being color-coded.

21. The gown of claim 3, the at least one medical procedure gown comprising a neck binding coupled to the another body-covering portion, wherein the neck binding comprises another color-coding indicating that the procedure verification card is attached to the gown.

22. The gown of claim 21, wherein the another body-covering portion and the another color-coding are different in color.

23. The gown of claim 3, further comprising sleeves coupled to the another body-covering portion, wherein the sleeves terminate in cuffs.

24. The gown of claim 23, wherein the cuffs are color-coded.

25. The gown of claim 3, the at least one medical procedure gown manufactured from a non-woven fabric.

26. The gown of claim 3, the at least one medical procedure gown comprising a disposable gown.

27. The gown of claim 3, the at least one medical procedure gown comprising a water resistant lining.

28. The gown of claim 3, the at least one medical procedure gown comprising a reusable gown.

29. The gown of claim 3, the at least one medical procedure gown comprising one or more pockets.

30. The gown of claim 3, the another body-covering portion defining a body opening.

31. The gown of claim 3, further comprising one or more ties attached to the another body-covering portion.

32. The gown of claim 3, the another body-covering portion comprising a single piece of material.

33. The gown of claim 3, further comprising one or more sleeves coupled to the another body-covering portion by one of stitching, ultrasonic sealing, glue, or tape.

34. The gown of claim 1, the procedure verification card comprising an indicator.

35. The gown of claim 34, the indicator comprising taking a time out to verify a correct patient.

36. The gown of claim 34, the indicator comprising taking a time out to verify a correct procedure.

* * * * *